United States Patent [19]

Seike et al.

[11] Patent Number: 4,607,619

[45] Date of Patent: Aug. 26, 1986

[54] LOCKING MECHANISM FOR AN ENDOSCOPE

[75] Inventors: Noboru Seike; Masatoshi Teranishi; Minoru Sakai, all of Hokkaido, Japan

[73] Assignee: Snow Brand Milk Products, Co., Ltd., Sapporo, Japan

[21] Appl. No.: 705,761

[22] Filed: Feb. 26, 1985

[30] Foreign Application Priority Data

Feb. 28, 1984 [JP] Japan ................................ 59-36848

[51] Int. Cl.⁴ .............................................. A61B 1/00
[52] U.S. Cl. .................................................... 128/4
[58] Field of Search .......................... 128/4, 3, 5, 6

[56] References Cited

U.S. PATENT DOCUMENTS

| | | | |
|---|---|---|---|
| 1,127,948 | 2/1915 | Wappler | 128/7 |
| 1,880,551 | 10/1932 | Wappler | 128/7 |
| 4,369,768 | 1/1983 | Vucovic | 128/6 |
| 4,538,594 | 9/1985 | Boebel et al. | 128/6 |

*Primary Examiner*—William H. Grieb
*Attorney, Agent, or Firm*—Flynn, Thiel, Boutell & Tanis

[57] ABSTRACT

In an endoscope, there are provided in a manipulating terminal of an optical visual pipe thereof an eyepiece member, a light-guide, various operative instrument channels and a handling forceps channel. Further, on the handling forceps channel are mounted a gas feeding pipe and a locking mechanism for locking a handling forceps.

2 Claims, 8 Drawing Figures

FIG. 5
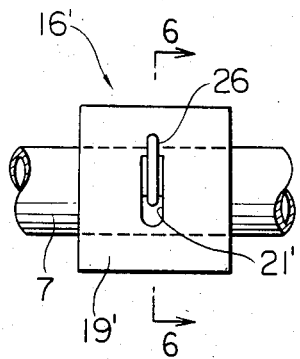
FIG. 6  FIG. 7
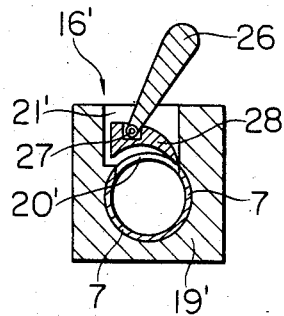 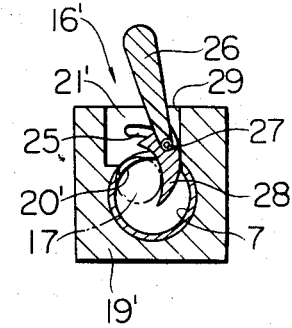
FIG. 8
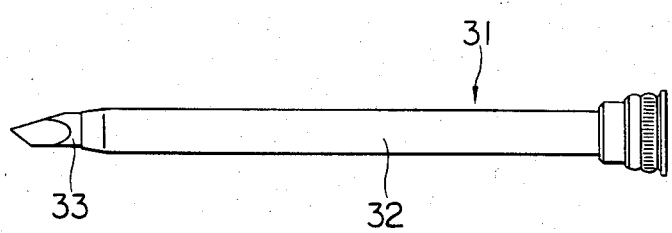

LOCKING MECHANISM FOR AN ENDOSCOPE

BACKGROUND OF THE INVENTION

1. Field of the Invention

The present invention relates to an endoscope, and more particularly to one provided with in a manipulating terminal of an optical visual pipe thereof an eyepiece member, a light-guide mounting member, an operative instrument inserting member and a handling forceps inserting member.

2. Description of the Prior Art

Hitherto, in this kind of endoscope there are provided: a light-guide for guiding a light from a light source mounted on the light-guide mounting member of the optical visual pipe to a desired portion (hereinafter referred to simply as the organ) of an internal organ in the abdominal cavity or in the thorax; an image-guide for guiding an image of the organ illuminated with the light to the eyepiece member; and an operative instrument channel for guiding an operative instrument and handling forceps to the organ, which instrument and forceps are inserted from the operative instrument inserting member and the handling forceps inserting member, respectively.

In use, the technical expert manipulates the operative instrument or the handling forceps while he observes the organ illuminated with the light. For example, in case that he catches the organ by the handling forceps, a locking operation thereof must be performed manually by an assisting technical expert. Also, in case that he performs an injection of a gas into the organ such as the uterus, since other instruments must also be used in addition to the endoscope, a number of technical experts are required to assist him in performing various operations such as an inspection of an inside of the abdominal cavity, a surgical operation or a surgical treatment of the various organs, an extracting operation of a specimen and so on. Such a need for a number of assisting technical experts and a complex operating procedure are demerits of the conventional endoscope.

SUMMARY OF THE INVENTION

Therefore, it is an object of the present invention to eliminate the above-mentioned demerits inherent in the conventional endoscope so as to provide an improved endoscope which enables the various kinds of the operations such as: the inspection of the inside of the abdominal cavity; the surgical operation or treatment of the various the organs; the extracting operation of a specimen and so on; to be performed by a small number of technical experts and as a result thereof, enables the technical experts or the surgeons to broaden their operable area so as to perform their operation neatly and very speedily.

The above object of the present invention can be accomplished in accordance with the present invention by providing a locking mechanism for locking the handling forceps and a gas injection member, in the handling forceps inserting member of the conventional endoscope. Namely, in the endoscope of the present invention, it is possible to eliminate the assisting technical experts for locking the handling forceps by providing a locking mechanism, and in addition to this, it is possible to eliminate a need for a separate gas injection apparatus and the assisting technical expert for operating the same by providing a gas injection member.

Since the endoscope of the present invention has the above-mentioned construction, it is possible to perform various kinds of operations accurately and easily due to its ability to maintain a distance between the organ to be operated on and the eyepiece member thereof at a certain level by means of a locking mechanism which locks the handling forceps, relative to the case where the technical expert locks the handling forceps manually. Moreover, in the endoscope of the present invention, since there is provided a gas injection member, it is possible to perform a local gas injection operation in contrast with the conventional gas injection apparatus. As a result, it is possible to avoid the fear of causing damage to the peritoneum, with the use of the endoscope of the present invention, and this constitutes one of features of the present invention.

In addition to the above feature of the present invention, the endoscope of the present invention has other features in that it is very easy to operate due to not requiring the conventional type of trocar having a complex gas injection apparatus for use with a large animal and also in that it is very effective for use in transplanting an embryo and for use in extracting an ovum in an Ovarian Follicle.

BRIEF DESCRIPTION OF THE DRAWINGS

In the drawings:

FIG. 5 is a side elevation of another type of a locking mechanism which differs from one shown in FIGS. 3 and 4;

FIG. 6 is a cross-sectional view taken along the line 6—6 of FIG. 5 showing the operative condition;

FIG. 7 is a view similar to FIG. 6 and showing the locking mechanism in the locking position;

FIG. 8 is a front view of a trocar employed with the endoscope of the present invention.

DESCRIPTION OF THE PREFERRED EMBODIMENTS

Figure 1:
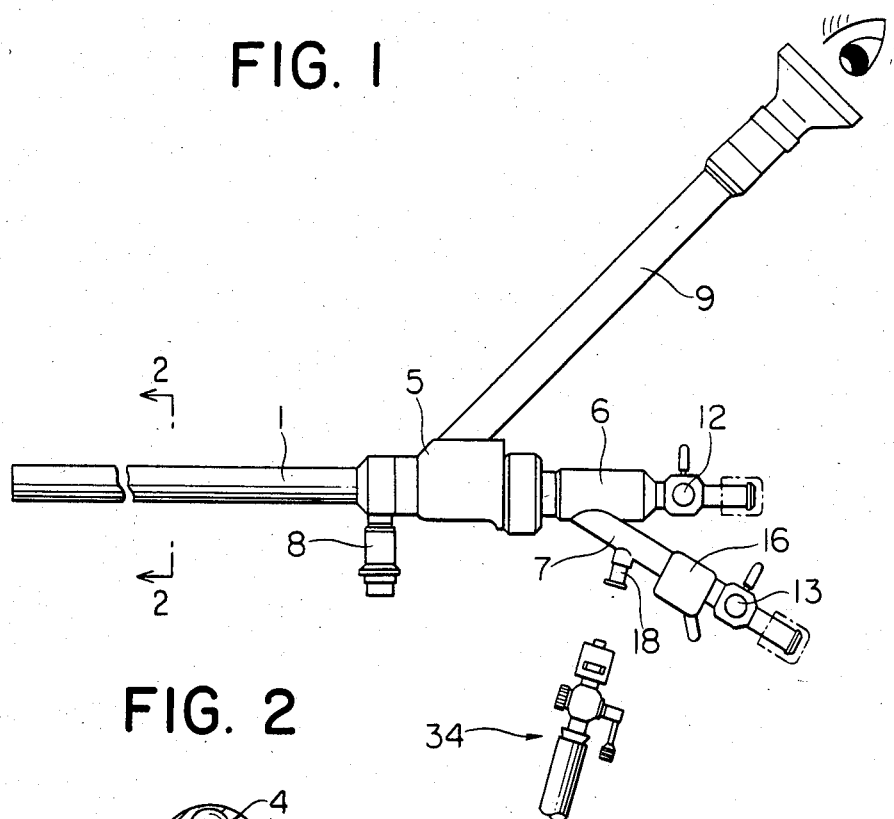
FIG. 1 is a partially cut away side elevation of an embodiment of the endoscope of the present invention.
Figure 2:
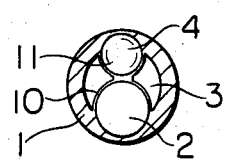
FIG. 2 is an enlarged cross-sectional view taken along the line 2—2 of FIG. 1.

In FIG. 1, reference numeral 1 designates an optical visual pipe inside of which is longitudinally partitioned by partitions 10, 11 into an operative instrument channel 2 for guiding an operative instrument, a light-guide 3 for illumination and an image-guide 4.

To a manipulating terminal 5 of the optical visual pipe 1 are attached an operative instrument inserting member 6, a handling forceps inserting member 7 branched off from the operative instrument inserting member 6, a light-guide 3 mounting member 8 and an eyepiece member 9 each of which members has a tubular shape. The channel 2 and inner holes of the inserting members 6, 7 are interconnected with each other; so are the light-guide 3 and inner hole of the light-guide mounting member 8; and so are the inner hole of the eyepiece member 9 and the image-guide 4, respectively. Reference numerals 12 and 13 designate cocks which are provided in the inserting members 6 and 7, respectively.

The above-mentioned endoscope of the present invention has the substantially the same construction as that of the conventional type of endoscope except that the gas injection member 18 and the locking mechanism 16 or 16' for locking handling forceps 17 are provided in the handling forceps inserting member 7 of the present invention.

Figure 3:
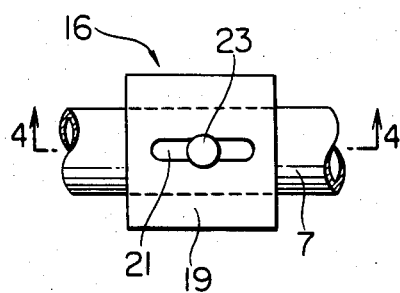
FIG. 3 is an enlarged side elevation of the locking mechanism for fixing the forceps.
Figure 4:
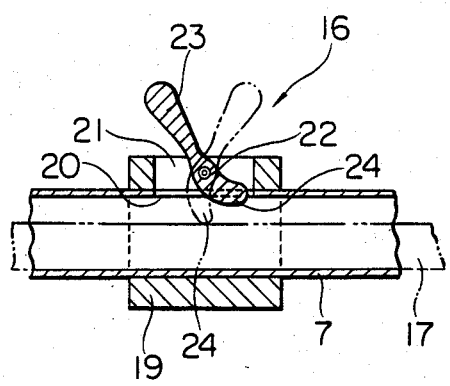
FIG. 4 is a cross-sectional view taken along the line 4—4 of FIG. 3.

An embodiment of the locking mechanism 16 is shown in FIGS. 3 and 4 and another embodiment thereof is shown in FIGS. 5 to 7.

The locking mechanism has a casing 19 in which the forceps inserting member 7 is inserted. A slit 20, which extends in a longitudinal direction of the forceps inserting member 7, is formed in a portion of the inserting member 7, which portion is inserted in the casing 19. In a portion of the casing 19, which portion corresponds to the slit 20, there is provided another slit 21 likewise. An axle 22 is provided between both side walls of the slit 21, and by means of the axle 22 a lever 23 is pivotally supported in its middle portion.

In use, a trocar 31 pierces into the abdominal cavity or into the thorax with the use of a point of its inner needle 33, and then the inner needle 33 is removed from an outer tube 32 of the trocar 31 while the outer tube 32 is held as it is.

Thereafter, the optical visual pipe 1 of the endoscope is inserted into the outer tube 32, and then the cocks 12 and 13 are closed so that a gas injection operation in the abdominal cavity is performed by injecting a gas from the gas feeding member 34 into the abdominal cavity through the gas injection member 18 and the operative instrument channel 2.

After completion of this operation, the light-guide 3 is mounted on the light-guide mounting member 8 and a light source (not shown) is turned on so as to inspect the organ illuminated with the light from the light source. Then, the cock 13 is opened to insert the handling forceps 17 into the handling forceps inserting member 7, which forceps 17 reaches the organ through the operative instrument channel 2 and then catches the organ. When the handling forceps 17 catches the organ, the lever 23 is turned from its unlocking position shown with a solid line in FIG. 4 to its locking position shown with a broken line in the same FIG. 4 so as to press the handling forceps 17 against the inner wall of the inserting member 7 thereof to lock the forceps 17 in this position.

Then the cock 12 is opened to insert various operative instruments into the abdominal cavity through the operative instrument inserting member 6 and the operative instrument channel 2 so as to perform a necessary operation in the peritoneal cavity, which operation may include a gas injection operation with the use of the gas injection member 18, if necessary.

As shown in FIGS. 5 to 7, a locking mechanism 16' is different from the above-mentioned locking mechanism 16 in that slits 20' and 21' provided in the inserting member 7 and a casing 19' respectively are disposed at right angles to the longitudinal axis of the inserting member 7, in both side walls of which slit 21' are provided arch-like grooves 25 in which opposite ends of a pin 27 attached to a front end of a lever 26 are slidably mounted. Curved pressing member 28 is pivotally mounted on the pin 27. In such a construction, generally the pressing member 28 is positioned in the unlocking position as shown in FIGS. 5 and 6. Consequently, locking operation of the handling forceps 17 is performed by moving the lever 26 to a locking position as shown in FIG. 7. As a result of this movement of the lever 26, the pressing member 28 is pressed in its back surface by a side edge 29 of the slit 21' so as to press the handling forceps 17 against the inner wall of the inserting member 7 to lock the forceps 17. The remaining part of the construction of the locking mechanism 16' is quite the same as that of the former locking mechanism 16, and therefore, the repetition of the description thereof is avoided.

Although particular preferred embodiments of the present invention have been disclosed in detail for illustrative purposes, it will be recognized that variations or modifications of the disclosed endoscope of the present invention, including the rearrangement of parts, lie within the scope of the present invention.

What is claimed is:

1. In an endoscope comprising an endoscopic pipe having a manipulating terminal thereon, said manipulating terminal having mounted thereon an eyepiece member, a light-guide mounting member, an instrument insertion member and a handling forceps insertion member, the improvement which comprises:

said handling forceps insertion member has a gas injection member and a locking mechanism mounted thereon, said locking mechanism being adapted for locking a handling forceps in position, said locking mechanism comprising a casing through which extends said handling forceps insertion member, said casing and said handling forceps insertion member having slits in corresponding portions thereof which slits communicate with each other, a lever and pivot means mounting the middle portion of said lever on said casing between the sidewalls of the slit thereof, so that said lever can be pivoted into said handling forceps insertion member, said lever having a front end portion which is adapted to lock in position a handling forceps which has been inserted in said handling forceps insertion member.

2. In an endoscope comprising an endoscopic pipe having a manipulating terminal thereon, said manipulating terminal having mounted thereon an eyepiece member, a light-guide mounting member, an instrument insertion member and an elongated handling forceps insertion member, the improvement which comprises:

said handling forceps insertion member has a gas injection member and a locking mechanism mounted thereon, said locking mechanism being adapted for locking a handling forceps in position, said locking mechanism comprising a casing through which extends said handling forceps insertion member, said casing and said handling forceps insertion member having lateral slits in corresponding portions thereof which slits communicate with each other and extend at a right angle to the longitudinal axis of said handling forceps insertion member, said slit in said casing having opposed side walls having arcuate grooves therein, a pin extending across said slit in said casing and having end portions slidably mounted in said grooves, a lever having a front end mounted on said pin for movement therewith, a pressing member mounted on said pin for pivotal movement so that said pressing member can be pivoted by said lever into said handling forceps insertion member, said lever having a pressing portion which is adapted to lock in position a handling forceps which has been inserted in said handling forceps insertion member.

* * * * *